US007511168B2

(12) United States Patent
Wei et al.

(10) Patent No.: US 7,511,168 B2
(45) Date of Patent: Mar. 31, 2009

(54) PROCESSES AND INTERMEDIATES FOR THE PREPARATIONS OF PROSTAGLANDINS

(75) Inventors: Shih-Yi Wei, 8F, No. 84, Sec. 2, Fu-Hsin S. Rd., Taipei (TW); Yu-Chih Yeh, 4F, No. 19, Ln 68, Ning-An St, Taipei (TW)

(73) Assignees: Shih-Yi Wei, Taipei (TW); Yu-Chih Yeh, Taipei (TW)

( * ) Notice: Subject to any disclaimer, the term of this patent is extended or adjusted under 35 U.S.C. 154(b) by 0 days.

(21) Appl. No.: 11/334,337

(22) Filed: Jan. 18, 2006

(65) Prior Publication Data
US 2007/0167641 A1    Jul. 19, 2007

(51) Int. Cl.
C07C 69/74     (2006.01)
C07C 233/00    (2006.01)
C07C 69/63     (2006.01)
C07D 307/00    (2006.01)
C07D 233/44    (2006.01)
C07D 265/30    (2006.01)
C07D 241/04    (2006.01)

(52) U.S. Cl. .................. 560/122; 564/189; 558/230; 549/302; 548/326.5; 544/106; 544/358

(58) Field of Classification Search ............... 554/119; 560/122; 564/189; 558/230; 549/302; 548/326.5; 544/106, 358
See application file for complete search history.

(56) References Cited

U.S. PATENT DOCUMENTS

| 4,013,695 | A |   | 3/1977  | Lin |
| 4,232,166 | A |   | 11/1980 | Wissner |
| 4,233,231 | A | * | 11/1980 | Floyd et al. ............... 556/12 |
| 4,272,629 | A |   | 6/1981  | Roberts |
| 4,536,592 | A |   | 8/1985  | Collins et al. |
| 4,983,753 | A | * | 1/1991  | Floyd, Jr. ................. 560/17 |
| 5,359,095 | A |   | 10/1994 | Resul |
| 5,661,178 | A |   | 8/1997  | Chen et al. |
| 6,852,880 | B2|   | 2/2005  | Ham et al. |
| 2005/0154220 | A1 | | 7/2005 | Clissold et al. |
| 2005/0209337 | A1 | | 9/2005 | Gutman et al. |
| 2006/0079693 | A1 | | 4/2006 | Suen et al. |

FOREIGN PATENT DOCUMENTS

| EP | 0 267 605   | 5/1988 |
| WO | WO 93/00329 | 1/1993 |
| WO | WO 02/096898 | 12/2002 |

OTHER PUBLICATIONS

March's Organic Chemistry. Reactions, Mechanisms, and Structures. 5th ed. NY Wiley & Sons, Inc. 2001, p. 869.*
Gooding An Expedient Triply convergent synthesis of Prostaglandins. J. Org.chem. 1990,55, 4209-4211.*
Patent Abstracts of Japan of 09020788 dated Jan. 21, 1997.
Corey, E.J. et al. "Total Synthesis of Prostaglandins $F_{2a}$ and $E_2$ the Naturally Occurring Forms" *Journal of the American Chemical Society* (1970) vol. 92, No. 2, pp. 397-398 XP-002386523.
Lai, S. et al. Enantioselective Synthesis of 12-epi-$PGF_{2a}$ and 12,15-diepi-$PGF_{2a}$ *J. Org. Chem.* (1999) vol. 64, pp. 7213-7217 XP-002386524.
Database CA [Online] Chemical Abstract. Howard, C. et al. "Total Synthesis of (.+-.)-Prostaglandin E2 Methyl Ester . . ." *Journal of the Chemical Society, Perkin Transactions : Organic and Bio-Organic Chemistry* (1981) vol. 7, pp. 2049-2054 XP-002386565 retrieved from STN.
Itoh, T. et al. "Simple Preparation of the Optically Active gamma-Hydroxy Vinylstannanes Using Lipase-Catalyzed Hydrolysis" *Chemistry Letters* (1991) vol. 2, pp. 217-218 XP-002386525.
Database Crossfire Beilstein. Tolstikov, G.A. et al. "Beilstein Institut zur Forderung der Chemischen Wissenschaften" *Chem. Nat. Compd.* (1985) vol. 21, No. 5, pp. 570-578 XP-002386566.
Tolstikov, G.A. et al. "Regio- and Stereoselective Hydrostannylation of 3-Hydroxy-4-phenoxy-1 . . ." *Synthesis* (1986) vol. 6, pp. 496-499 XP-002386526.

(Continued)

Primary Examiner—Jafar Parsa
(74) Attorney, Agent, or Firm—Ladas and Parry LLP

(57) ABSTRACT

The present invention provides novel processes for the preparation of a cyclopentanone of Formula II and a lactone of Formula I, which are useful in the production of prostaglandins:

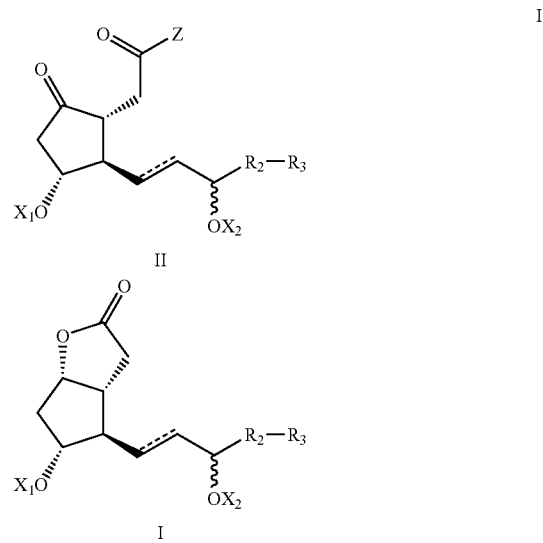

wherein Z, $R_2$, $R_3$, $X_1$, $X_2$, and ----- are as defined in the specification.

The invention also provides novel enantiomerically enriched compounds.

5 Claims, No Drawings

OTHER PUBLICATIONS

Gooding, O.W. et al. "Triply Convergent Synthesis of 15-(Phenoxymethyl) and 4,5-Allenyl Prostaglandins. Preparation of an Individual Isomer of Enprostil" *J. Org. Chem.* (1993) vol. 58, pp. 3681-3686 XP-002386527.

Database CA [Online] Chemical Abstract. Kalnins, A et al. "Total Synthesis and Properties of Prostaglandins XXVI. Alkylation of Bicyclic Dihydropyridazinones" *Latvijas PSR Zinatnu Akademijas Vestis. Kimijas Serija* (1990) vol. 1, pp. 78-87 XP-002386567 retrieved form STN.

Database CA [Online] Chemical Abstract. Kalnins, A. et al. "Total Synthesis and Properties of Prostaglandins. X. synthesis of .gamma.-oxy . . . " *Zhurnal Organicheskoi Khimii* (1988( vol. 24, No. 4, pp. 742-755 XP-002386568 retrieved from STN.

Database CA [Online] Chemical Abstract. Kudryashova, V.V. et al. "Synthesis of Methyl 3.alpha . . . " *Bioorganicheskaya Khimiya* (1986) vol. 12, No. 4, pp. 848-854 XP-002386569 retrieved from STN.

Database CA [Online] Chemical Abstract. Sakhartova, O.V. et al. "Comparative Calculation of Retention Values in Chromatogrpahy of Cyclopentane Derivatives on Silica Gel" *Zhurnal Analiticheskoi Khimii* (1985) vol. 40, No. 5, pp. 872-880 XP-002386570 retrieved from STN.

Database CA [Online] Chemical Abstract. Marino, J.P. et al. "Stereocontrolleed Synthesis of Prostaglandins from Cyclopentadiene Monoepoxide" *Journal of Organic Chemistry* (1984) vol. 49, No. 26, pp. 5279-5280 XP-002386571 retrieved from STN.

Database CA [Online] Chemical Abstract. Sakhartova, O.V. et al. "Chromatogrpahy of Prostaglandins, Their Analogs and Intermediates . . . " *Latvijas PSR Zinatnu . . .* (1983) vol. 5, pp. 556-563 XP-002386572 retrieved from STN.

Chen, S.L. et al. "Prostaglandins and Congeners. 19. Vinylstannanes: Useful Organometallic Reagents for the Synthesis of Prostaglandins and Prostaglandin Intermediates" J. Org. Chem. (1978) vol. 43, No. 18, pp. 3450-3454 XP-002386528.

R. Noyori, M. Suzuki: *Protaglandin Syntheses by Three-Component Coupling*: Agnew. Chem. INt. Ed. Engl. 23: (1984): pp. 847-876.

S. Okamoto, Y. Kobayashi, H. Kato, K. Hori, T. Takahashi, J. Tsuji, F. Sato: *Prostaglandin Synthesis via two-component Coupling . . .* J. Org. Chem. 1988, 53, pp. 5590-5592.

Lola (Zh. Org. Khim 1985, 21 (10), 2091).

M. Suzuki, A. Yanagisawa, R. Noyori: *The Three-Component Coupling Synthesis of Prostaglandins*: J. Am Chem. Soc. 1988: 110, pp. 4718-4726.

C. Sih, J. Heather, R. Sood, P Peruzzotti, L. Lee, S. Lee: *Asymmetric Total Synthesis of (-)-Prostaglandin $E_1$ (-)-Prostaglandin $E_2^{1:J}$*: J. Am. Chem Soc., 1975 97, pp. 865-867.

P. Baraldi, A. Barco, S. Benetti, G. Pollini, D. Simoni, V. Zantrato: *stereospecific nitromethane conjugate addition to 4-oxygenated-2-substituted-cyclo pent-2- . . .* : Tetrahedron, 1987 , 43, 4669-4678.

* cited by examiner

PROCESSES AND INTERMEDIATES FOR THE PREPARATIONS OF PROSTAGLANDINS

FIELD OF THE INVENTION

The present invention relates to novel processes and intermediates for the preparations of Prostaglandins and the derivatives thereof.

BACKGROUND OF THE INVENTION

Prostaglandins and the derivatives thereof have various biological actions, such as a vasodilating action, a prophlogistic action, an inhibitory action of blood platelet aggregation, a uterine muscle contraction action, an intestine contraction action and a lowering action of intraocular pressure, and can be used in the preparation of medicaments for treatment or prevention of myocardial infarction, angina pectoris, arteriosclerosis, hypertension, or duodenal ulcer, which are valuable for human as well as veterinary applications.

For the last few decades, many academic researchers and industrial organizations have made tremendous efforts in exploring various key intermediates as well as innovative processes for efficient and cost-saving synthesis of Prostaglandins (Collines, P. W. et. al., 1993, *Chem. Rev.* 93, 1533).

Specifically, lactones of Formula I are very important late-stage intermediates for synthesis of Prostaglandin $2\alpha$ compounds.

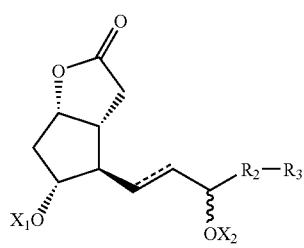

I

I-1: ═══being a double bond, $X_1$ and $X_2$ being protecting group

I-2: ═══being double bond, $X_1$ and $X_2$ being H

I-3: ═══being single bond, $X_1$ and $X_2$ being protecting group or H

For example, Lactones of Formula I-1 or I-2, wherein $R_2$ is methylene and $R_3$ is n-butyl, are key intermediates for the synthesis of nature Prostaglandin $F_{2\alpha}$, $E_2$ and $I_2$, as reported in E. J. Corey, et al, *J. Am. Chem. Soc.* 1970, 92, 397; and *J. Am. Chem. Soc.* 1977, 99, 2006.

Lactones of Formula I-1 or I-2, wherein $R_2$ is methylene and $R_3$ is benzyl, are advanced intermediates for the synthesis of Bimatoprost, as disclosed in USP 2005/0209337.

Lactones of Formula I-1 or I-2, wherein $R_2$ is —$CH_2O$— and $R_3$ is a substituted phenyl, are intermediates for the synthesis of (+)-Cloprostenol, Travoprost and (+)-Fluprostenol, as disclosed in EP 0362686 and USP 2005/0209337.

Lactones of Formula I-3, wherein $R_2$ is methylene and $R_3$ is benzyl, are intermediates for the synthesis of Latanoprost, as disclosed in U.S. Pat. No. 5,359,095.

In industry, the above mentioned Lactones of Formula I have been prepared from a famous intermediate III (the so-called Corey aldehyde) via the route depicted below in Scheme 1:

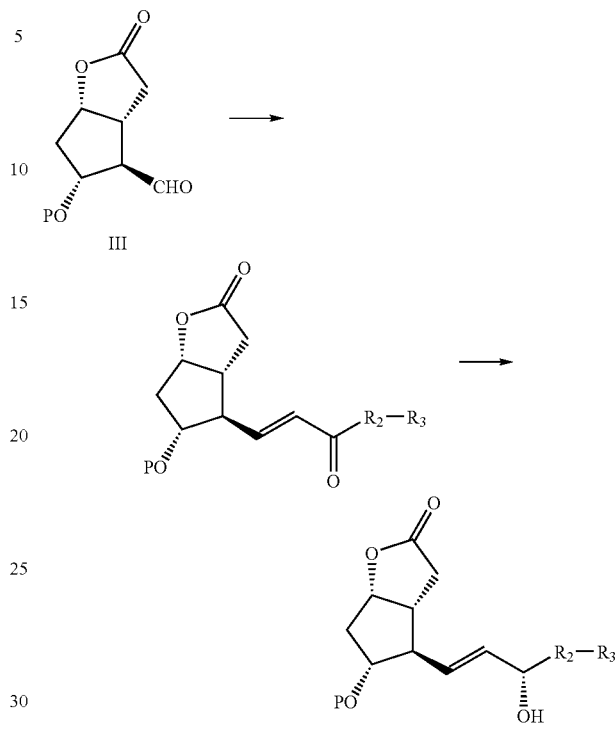

Scheme 1 wherein P is a protecting group; and $R_2$ and $R_3$ are as defined above.

The synthesis of Corey aldehyde III (Corey's process) consists of more than 12 reaction steps in a linear route with the use of cyclopentadiene as the starting material. In Corey's process, not only is it difficult to proceed with the production reproducibly but the final target compound is usually obtained in a low yield. In addition, the major drawback of the Corey's process is associated with the poor selectivity toward the reduction of the 15-ketone functional group on the ω-side chain (Scheme 1), which often results in a considerable amount of the 15-β isomer generated as a major impurity. [See Corey, et. al., 1987, *J. Am. Chem. Soc.*, 109, 7925; Corey, et. al., 1972, *J. Am. Chem. Soc.*, 94, 8616; Corey, et. al., 1971, *J. Am. Chem. Soc.*, 93, 1491; and Noyori, et. al., 1979, *J. Am. Chem. Soc.*, 101, 5843]. In order to remove the 15-β isomer, it is necessary to utilize chromatography in the Corey's process for the separation of the isomers having slight differences in the $R_f$ values.

Given the above, conventional approaches for producing Lactones of Formula I encountered problems to be solved. The objective of the invention is to provide a simpler as well as a cost-effective synthesis route for Lactones of Formula I to eliminate the problems associated with the conventional processes, either in the aspect of a number of synthetic steps or in the necessity of removing unwanted isomers.

SUMMARY OF THE INVENTION

In one aspect, the present invention provides novel processes for the preparation of the key intermediates of Formula I, which are useful in the production of prostaglandins:

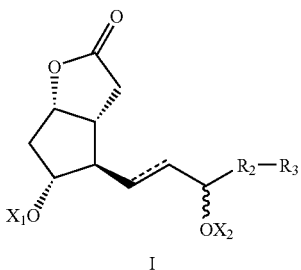

wherein $R_2$ is a single bond or a $C_{1-4}$-alkylene or a group of formula —$CH_2O$—; $R_3$ is a $C_{1-7}$-alkyl or an aryl or an aralkyl, each of which is unsubstituted or substituted by a $C_{1-4}$ alkyl, a halogen and a trihalomethyl; $X_1$ and $X_2$ are protecting groups for the hydroxy group or H, and ===== is a single or double bond.

In another aspect, the invention provides novel enantiomerically enriched Cyclopentanones of Formula II,

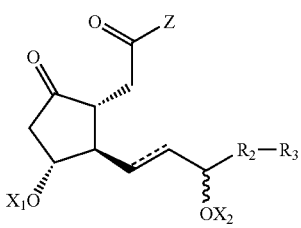

wherein Z is an arbitrary group that does not participate in a coupling and deprotection reactions but acts as a leaving group in a reduction/lactonization reaction; $R_2$, $R_3$, $X_1$, $X_2$ and ===== are defined as above, and processes for preparing the same.

In yet another aspect, the invention provides a novel enantiomerically enriched lactone and novel enantiomerically enriched compounds useful for the production of the compounds of Formula I.

DETAILED DESCRIPTION OF THE INVENTION

Definition

The term "alkyl" used herein refers to a straight or branched hydrocarbon group containing 1 to 30 carbon atoms, such as methyl, ethyl, isopropyl, tert-butyl, and the like; or a cyclic saturated hydrocarbon group having 3 to 10 carbon atoms, such as cyclopropyl, cyclopentyl, cyclohexyl, menthyl, and the like.

The term "lower alkyl" used herein refers to an alkyl containing 1 to 6 carbon atoms such as methyl, ethyl, propyl, and the like.

The term "alkenyl" used herein refers to a straight or branched hydrocarbon group containing 3 to 20 carbon atoms and one or more carbon-to-carbon double bonds, such as pentenyl, propenyl, and the like; or a cyclic unsaturated hydrocarbon group having 5 to 20 carbon atoms and one or more carbon-to-carbon double bonds, such as cyclopentenyl, cyclohexenyl, and the like.

The term "alkynyl" used herein refers to a straight or branched hydrocarbon group containing 3 to 20 carbon atoms and one or more carbon-to-carbon triple bonds such as pentynyl, propynyl, and the like; or a cyclic unsaturated hydrocarbon group having 6 to 20 carbon atoms and one or more carbon-to-carbon triple bonds.

The term "aryl" used herein refers to a monocyclic or polycyclic aromatic hydrocarbon radical, such as phenyl, naphthyl, anthryl, phenanthryl and the like. The aryl may optionally be substituted with one or more substituents, including but not limited to, a halogen, an alkoxyl, a thioalkoxyl, an alkyl, and an aryl.

The term "aralkyl" used herein refers a straight or branched hydrocarbon containing 1 to 20 carbon atoms and one or more aryl group as described above, such as benzyl, benzhydryl, fluorenylmethyl, and the like.

Each of the above mentioned alkyl, alkenyl, alkynyl, aryl, and aralkyl may optionally be substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl, pyrrolidinonyl, and the like.

The term "protective group" has the meaning conventionally defined in organic synthetic chemistry, i.e., a group capable of protecting a functional group or moiety of a compound against the attacks of a chemical reaction. Examples of the protective group include, but are not limited to, methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, and $SiR_a R_b R_c$ wherein $R_a$, $R_b$ and $R_c$ are each independently a $C_{1-4}$ alkyl, phenyl, benzyl, a substituted phenyl, or a substituted benzyl.

In the depiction of the compounds given throughout this description, a thickened taper line ( ~~~ ) indicates a substituent which is in the beta-orientation (above the plane of the molecule or page), a broken flare line ( ···· ) indicates a substituent which is in the alpha-orientation (below the plane of the molecule or page), and a wavy line ( ~~~ ) indicates a substituent which is either in the alpha- or beta-orientation or in a combination of these orientations.

Aspects of the Invention

In the present invention, a novel approach for the synthesis of a Lactone of Formula I is depicted in scheme 2. All reactants are used in their enantiomerically enriched form, typically with an optical purity of higher than 90% e.e.

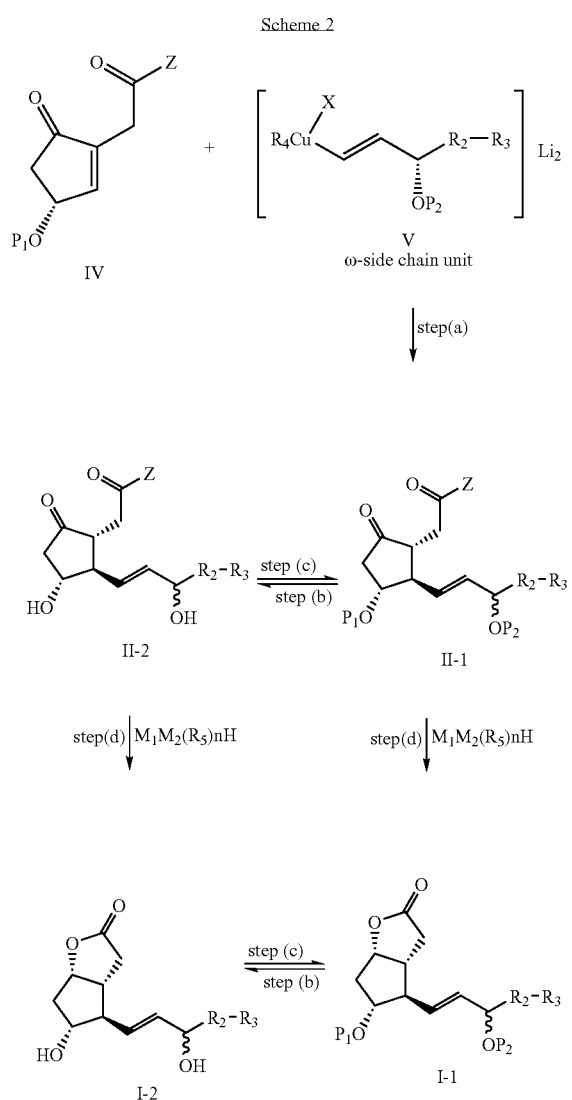

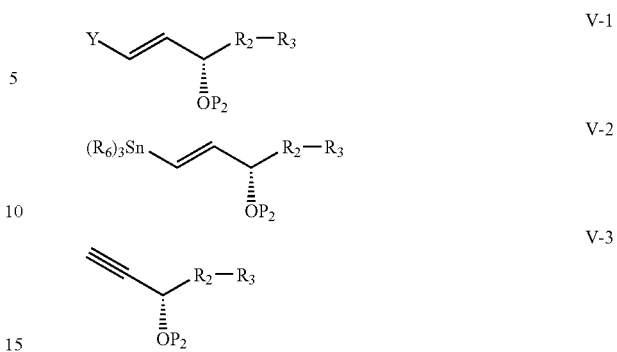

wherein Y is a halogen; $R_6$ is a lower alkyl; $R_2$, $R_3$, and $P_2$ are as defined above, as described in Chen, et. al., 1978, *J. Org. Chem.*, 43, 3450, U.S. Pat. No. 4,233,231, U.S. Pat. No. 4,415,501 and U.S. Pat. No. 6,294,679; with an optically active Cyclopentenone of Formula IV, the preparation of which has been disclosed in the co-pending patent application filed on the even date and entitled "PROCESSES FOR THE PREPARATIONS OF OPTICALLY ACTIVE CYCLOPENTENONES AND CYCLOPENTENONES PREPARED THEREFROM."

Subsequently, the reaction is quenched with a base, e.g., ammonium hydroxide or the like, and subjected to a work-up procedure conducted in a conventional manner. The resultant crude product can be purified by a conventional method, such as column chromatography, or the unpurified product can be directly used in the next reaction.

According to the embodiments of the invention, the substituent Z in the above-mentioned Formulae is $—OR_1$, $—N(R_1)_2$, or $—SR_1$, where $R_1$ at each occurrence is independently an alkyl, an alkenyl, an alkynyl, an aryl or an aralkyl group each of which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, and carbonyl or a heterocyclic group selected from the group consisting of pyridinyl, thiophenyl, furanyl, imidazolyl, morpholinyl, oxazolinyl, piperidinyl, piperazinyl, tetrahydropyranyl, pyrrolidinyl and pyrrolidinonyl, or when Z is $—OR_1$, $R_1$ is a protecting group for the carboxyl group. Preferably, Z is $—OR_1$.

A. Preparation of Novel Cyclopentanones of Formula II-1

As shown in Step (a) of Scheme 2, a Cyclopentanone of Formula II-1 wherein Z is an arbitrary group that does not participate in coupling and deprotection reactions but acts as a leaving group in a reduction/lactonization reaction; $R_2$ is a single bond or a $C_{1-4}$-alkylene or a group of formula $—CH_2O—$; $R_3$ is a $C_{1-7}$-alkyl or an aryl or an aralkyl group, each of which is unsubstituted or substituted by a $C_{1-4}$-alkyl, a halogen, or a trihalomethyl; and $P_1$ and $P_2$ are the same or different protecting groups for the hydroxy group, are prepared by a coupling reaction, which is preferably performed at a temperature ranging from −100° C. to 40° C., of an enantiomerically enriched ω-side chain unit of a cuprate of Formula V (wherein $R_2$, $R_3$, and $P_2$ are as defined above; $R_4$ is a non-interfering group; and X is $—CN$, $—SCN$, $—OSO_2CF_3$, or $—S$-phenyl-) derived from a vinyl halide of Formula V-1, a vinyl stannane of Formula V-2 or an alkyne of Formula V-3, B. Preparation of Lactones of Formula I As shown in Step (d) of Scheme 2, a Cyclopentanone of Formula II-1 or II-2 is reduced/lactonized to form a Lactone of Formula I-1 or I-2 with a reducing agent of Formula Y:

$$M_1M_2(R_5)_nH \qquad Y$$

wherein $M_1$ is Li, K, or Na or absent; $M_2$ is Al or B; n is 2 or 3; and $R_5$ is hydrogen, an alkyl or an alkoxyl, in a suitable solvent. According to the present invention, the reducing agent is selected from sodium bis(2-methoxyethoxy)aluminum hydride, diisobutylaluminum hydride, lithium tri-tert-butoxyaluminohydride, a lithium tri-alkyl borohydride, a potassium tri-alkyl borohydride or a sodium tri-alkyl borohydride or a mixture thereof. Preferably, the reducing agent is lithium tri-sec-butylborohydride, lithium tri-amylborohydride, sodium tri-sec-butylborohydride, potassium tri-sec-butylborohydride, or potassium tri-amylborohydride or a mixture thereof. Most preferably, the reducing agent is lithium tri-sec-butylborohydride. The non-limiting, suitable solvent used in the above reaction can be selected from tetrahydrofuran, ether, toluene, hexane, or a mixture thereof. The reaction is carried out at a temperature ranging from −120° C. to the room temperature, preferably from −100° C. to −40° C. The reducing agent is used in an amount such that the substrates or the reactants are completely reacted as monitored by Thin Layer Chromatography (TLC). Upon completion of the reaction, the Lactone of Formula I-1 or I-2 can be isolated from the reaction mixture by a work-up procedure such as removing the excessive reducing agent, extraction, dehydration, concentration, and the like. The product may be further purified by column chromatography or by crystallization.

C. Deprotection of Cyclopentanones of Formula II-1 or Lactones of Formula I-1

As shown in Step (b) of Scheme 2, the Cyclopentanone of Formula II-2 and the Lactone of Formula I-2 are prepared by deprotecting a Cyclopentanone of Formula II-1 and a Lactone of Formula I-1, respectively. The conditions for carrying out such deprotection reactions are obvious to persons skilled in the art. For example, the Cyclopentanones of Formula II-1 wherein each of $P_1$ and $P_2$ is a triethylsilyl protecting group are dissolved in a suitable solvent, such as a solvent mixture of acetone and water in a volumetric ratio of 5 to 1, treated with a deprotecting agent such as hydrogen chloride, p-toluenesulfonic acid, or pyridium p-toluenesulfonate, and stirred at room temperature for 10 minutes to 10 hours to obtain the deprotected product of formula II-2.

The crude Cyclopentanone product of II-2 contains a small amount of stereoisomers generated from the conjugate addition reaction (coupling reaction), which can be further removed by column chromatography eluted with single solvent or a mixture of two or more of hexane, heptane, ethyl acetate, toluene, ether, and isopropyl alcohol.

Alternatively, the stereoisomers present in the crude product II-2 can be removed by the crystallization of the crude product. The crystallization is preferably carried out in a suitable organic solvent selected from ethyl ether, petroleum ether, isopropyl ethyl ether, butyl methyl ether, ethyl acetate, toluene, isopropyl ethyl ketone, methyl isobutyl ketone, hexane, heptane, isopropyl alcohol, methanol, ethanol, or acetic acid, or a mixture thereof.

D. Protection of Cyclopentanones of Formula II-2 or Lactones of Formula I-2

Both the protected Lactone I-1 or non-protected Lactone I-2, as shown in Scheme 2, can be further subjected to a reduction reaction with diisobutylaluminum hydride (DIBAL) as well as a Wittig reaction to obtain the final target Prostaglandin. However, it is preferable to use the protected Lactone I-1 to avoid excessive consumption of DIBAL as well as Wittig reagents for reacting with the hydroxyl groups.

As illustrated in Scheme 2, step (c) is performed to protect the Cyclopentanone of Formula II-2 or Lactone of Formula I-2. Suitable protective groups used are trialkylsilyl, tetrahydropyranyl (THP), and the like. Suitable reaction conditions are obvious to persons skilled in the art. For example, the Lactone of Formula I-2 that is dissolved in an appropriate solvent selected from tetrahydrofuran, ethyl acetate, toluene, or dimethylformamide, or a mixture thereof, can be reacted with more than 2 mol. eq. of a base such as a triakylamine or imidazole as well as about 2 mol. eq. of tert-butyldimethylsilyl chloride at a temperature ranging from about 0 to 80° C. Subsequently, a work-up procedure, such as filtration, extraction, dehydration, and concentration is employed to obtain a protected Lactone of Formula I-1. According to the present invention, a Lactone of the Formula I-1a having a high purity in its crystalline form was unexpectedly and surprisingly obtained:

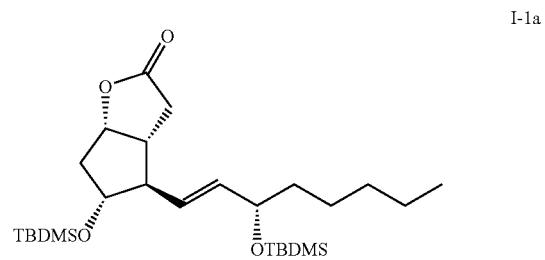

I-1a

E. Synthesis of 13,14-dihydrolactones of Formula I-3

Lactones of Formula I-3, as shown in Scheme 3 below, which are useful for the synthesis of 13,14-dihydro-Prostaglandin $F_2$alpha, especially for the synthesis of Latanoprost, may be prepared via one of the routes as described below and illustrated in Scheme 3:

(i) Conducting a coupling reaction of the co-side chain unit of a cuprate of Formula VI, which may be prepared according to the method disclosed in U.S. Pat. No. 6,852,880, with a Cyclopentenone of Formula IV to obtain a protected Cyclopentanone of Formula II-3, which is further subjected to deprotection and reduction/lactonization reaction to obtain an unprotected Lactone of Formula I-3;

(ii) Reacting a Cyclopentenone of Formula IV with a cuprate of Formula V to obtain a Cyclopentanone of Formula II, which is further subjected to deprotection, hydrogenation, and reduction/lactonization reactions as depicted in steps (e) and (d) to obtain an unprotected Lactone of Formula I-3; or (iii) Converting the Cyclopentanone of Formula II obtained according to the route recited in Item (ii) to a protected Lactone of Formula I, which is further deprotected and hydrogenated or hydrogenated without being deprotected to obtain an unprotected or a protected Lactone of Formula I-3.

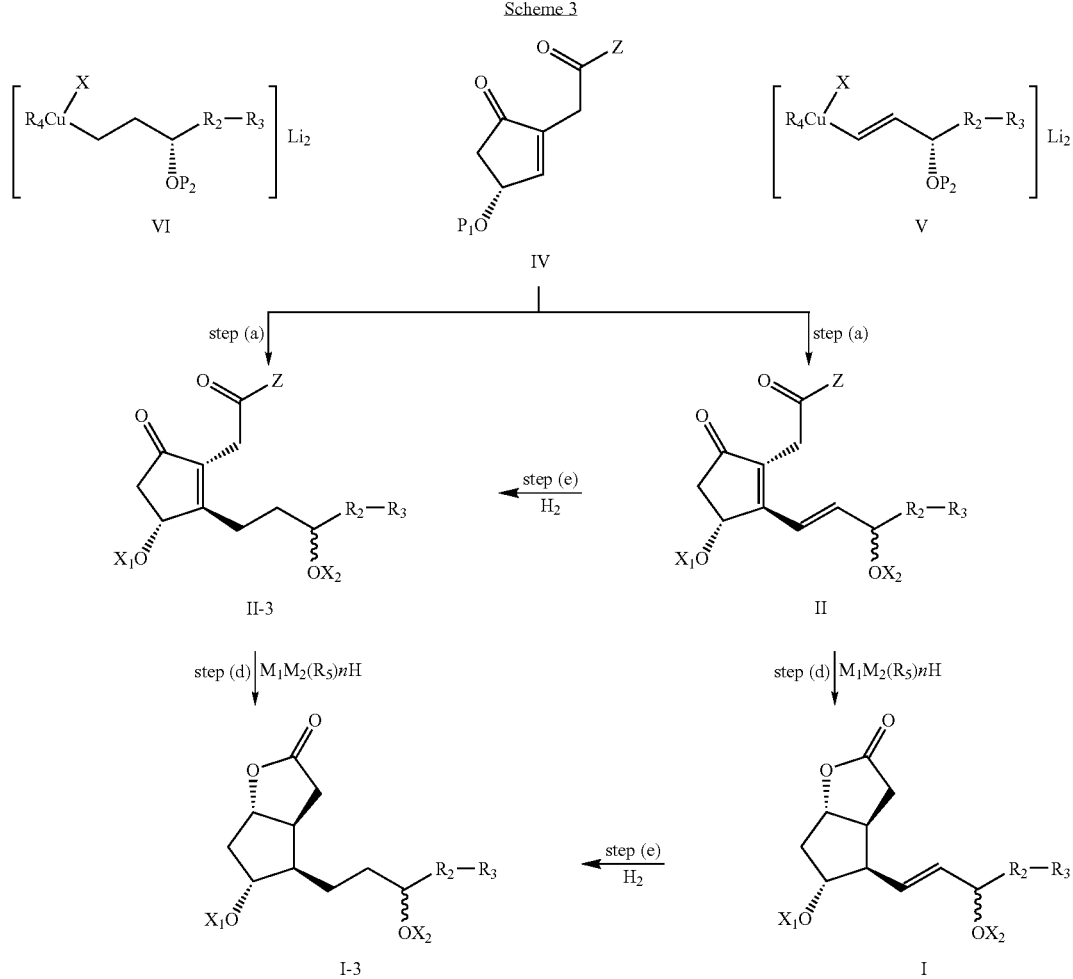

Scheme 3 wherein Z, $R_4$, $R_5$, $M_1$, $M_2$, n, $P_1$, $P_2$, $X_1$ and $X_2$ are as defined above.

The hydrogenation reaction of step (e) in Scheme 3 is performed under hydrogen in the presence of a hydrogenation catalyst and a suitable base/electrophile reagent in a suitable solvent. Suitable hydrogenation catalyst contains a metal selected from the group consisting of palladium, platinum, rhodium, and nickel and a mixture thereof. Examples of the catalyst include Pd—C, Pt—C, and Ni. Suitable solvent can be selected from tetrahydrofuran, ethyl acetate, ethanol, or toluene, or a mixture thereof.

The Lactone of Formula I is then subjected to a semi-reductive reaction with diisobutyl aluminium hydride (DIBAL) as illustrated in Step (e) followed by Wittig reaction to produce a Prostaglandin, particularly $PGE_2$ and $PGF_2\alpha$ series. The details regarding DIBAL and Wittig reactions are available from prior art documents, such as Lee et. al., 1978, *J. Chem. Soc.*, Perkin trans I 1179; EP-A-0639563; Corey et. al., 1969, *J. Am. Chem. Soc.*, 91, 5675; and *J. Am. Chem. Soc.*, 1972, 94, 8616.

The present invention not only provides a simple and easy approach for the synthesis of Prostaglandins but solves the problems regarding the generation of excessive 15β-isomer, which results in the difficulty in the final purification as encountered in Corey's process. More importantly, the Cyclopentanone of Formula II prepared according to Scheme 3 can be further purified by crystallization or simple column chromatography to eliminate the 15β-isomer completely. In summary, the present invention provides a shortcut for the synthesis of Prostaglandins free of 15β-isomer.

F. Novel Compounds of Formula II

The invention further provides novel enantiomerically enriched compounds of Formula II

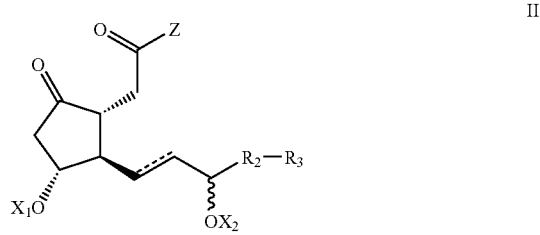

II having an optical purity of more than 95% enantiomeric excess; wherein Z is $OR_1$, and $R_1$, $X_1$, $X_2$, ⁓$R_2$ and $R_3$ are as defined above; with the proviso that the compound is not the one represented by any of formulae X-1, X-2, X-3, X-4 and X-5:

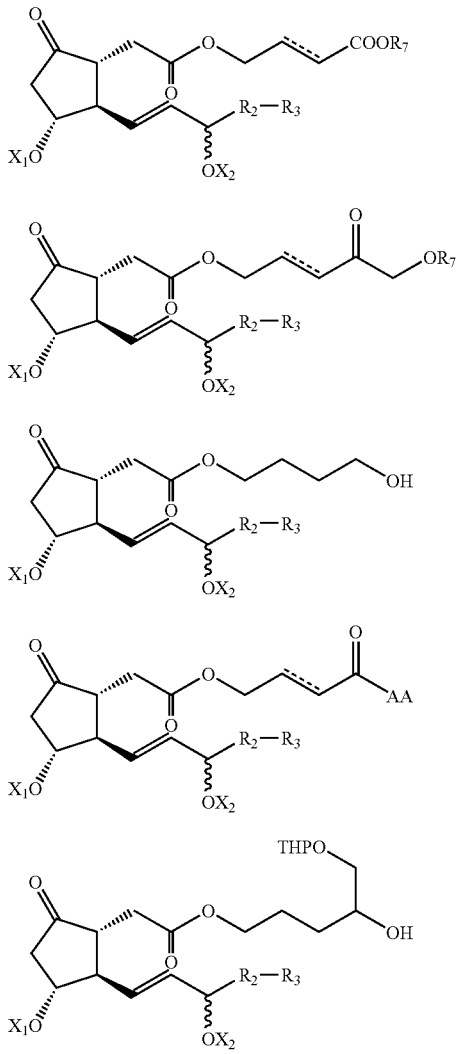

wherein $R_7$ is an arbitrary substituent; AA is hydrogen or an amino acid residue; and $X_1$, $X_2$, ═══$R_2$ and $R_3$ are as defined above.

According to one embodiment of the invention, $X_1$ and $X_2$ in Formula II are both hydrogen atoms; and $R_1$ is an alkyl, an alkenyl, or an alkynyl each of which is unsubstituted or substituted with one or more substituents selected from the group consisting of halogen, thioalkoxyl, thioaryloxy, alkylamino, and cyano, or a heterocyclic group selected from the group consisting of morpholinyl, oxazolinyl, piperidinyl, piperazinyl, tetrahydropyranyl, pyrrolidinyl and pyrrolidinonyl; or $R_1$ is an aryl which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, alkylaminocarbonyl, arylaminocarbonyl and carbonyl; or $R_1$ is an aralkyl, which is unsubstituted or substituted with one or more substituents selected from the group consisting of halogen, alkyl, aryl, alkoxyl, aryloxy, thioalkoxyl, thioaryloxy, alkylamino, cyano, alkoxycarbonyl, arylcarbonyl, alkylaminocarbonyl, arylaminocarbonyl and carbonyl. According to the more preferred embodiments of the invention, $R_1$ is $C_1$-$C_{10}$ alkyl, benzyl, naphthyl, or phenyl, each of which is unsubstituted or substituted with one or more substituents selected from the group consisting of halogen, alkyl, aryl, alkoxyl, aryloxy, thioalkoxyl, thioaryloxy, alkylamino, cyano, alkoxycarbonyl, alkylaminocarbonyl, and morpholinyl.

According to the most preferred embodiments of the present invention, the compound of Formula II is selected from the group consisting of:

Ethyl(1R,2R,3R)-3-hydroxy-2-[(3S)-hydroxy-1-octenyl]-5-oxo-cyclopentane acetate;

Benzyl(1R,2R,3R)-3-hydroxy-2-[(3S)-hydroxy-1-octenyl]-5-oxo-cyclopentane acetate;

2-Naphthyl(1R,2R,3R)-3-hydroxy-2-[(3S)-hydroxy-1-octenyl]-5-oxo-cyclopentane acetate;

(1'R,2'S,5'R)-Menthyl(1R,2R,3R)-3-hydroxy-2-[(3S)-hydroxy-1-octenyl]-5-oxo-cyclopentane acetate;

2-Cyanoethyl(1R,2R,3R)3-hydroxy-2-[(3S)-hydroxy-1-octenyl]-5-oxo-cyclopentane acetate;

3-Ethoxycarbonylphenyl(1R,2R,3R)-3-hydroxy-2-[(3S)-hydroxy-1-octenyl]-5-oxo-cyclopentane acetate;

4-Morpholineethyl(1R,2R,3R)-3-hydroxy-2-[(3S)-hydroxy-1-octenyl]-5-oxo-cyclopentane acetate;

Benzyl(1R,2R,3R)-3-hydroxy-2-[5-phenyl-(3S)-hydroxy-1-pentenyl]-5-oxo-cyclopentane acetate;

2-Naphthyl(1R,2R,3R)-3-hydroxy-2-[5-phenyl-(S)-hydroxy-1-pentenyl]-5-oxo-cyclopentane acetate;

(1'R,2'S,5'R)-Menthyl(1R,2R,3R)-3-hydroxy-2-[5-phenyl-(3S)-hydroxy-1-pentenyl]-5-oxo-cyclopentane acetate;

Ethyl(1R,2R,3R)-3-hydroxy-2-[5-phenyl-(3S)-hydroxy-1-pentenyl]-5-oxo-cyclopentane acetate;

Ethyl(1R,2R,3R)-3-hydroxy-2-[(3R)-hydroxy-4-(3-trifluoromethyl)phenoxy-1-butenyl]-5-oxo-cyclopenane acetate; and Ethyl(1R,2R,3R)-3-hydroxy-2-[5-phenyl-(3R)-hydroxypentanyl]-5-oxo-cyclopentane acetate.

G. Novel Enantiomerically Enriched Compounds of Formulae V-2a and V-2b

The invention further provides novel enantiomerically enriched compounds of Formulae V-2a and V-2b:

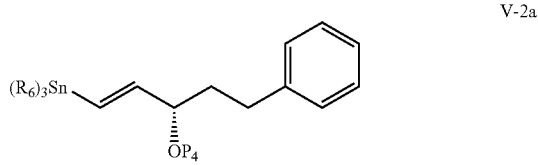

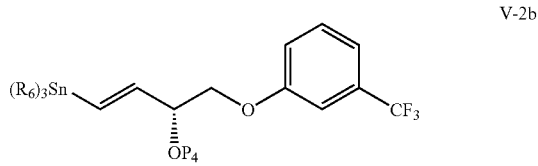

wherein $R_6$ is a lower alkyl, and $P_4$ is trimethylsilyl, triethylsilyl, tert-butyldimethylsilyl, tetrahydrofuranyl, tetrahydropyranyl, or 1-ethoxyethyl.

EXAMPLES

Example 1

4-[3-(Trifluoromethyl)phenoxy]-(3R)-triethylsilyloxy-1-butyne

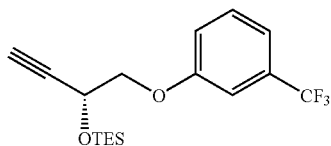

(3R)-4-[3-(Trifluoromethyl)phenoxy]-3-hydroxy-1-butyne (6.7 g, 29 mmol) and imidazole (2.96 g, 44 mmol) were dissolved in 100 ml ethyl acetate and the solution was cooled to about 5° C. Chlorotriethylsilane (6.3 ml, 38 mmol) was slowly added to the solution in 30 minutes at a temperature maintained at about 5-10° C. throughout the addition. The mixture was brought to room temperatures slowly. The precipitate was removed by filtration. Subsequently, the reaction mixture was washed with 50 ml saturated aqueous sodium bicarbonate solution twice, further washed with brine (50 ml), dried over anhydrous magnesium sulfate, filtered, and concentrated to obtain the crude product (13.2 g). The crude product was purified by distillation to give the (R)-silyl ether as colorless oil (9.1 g, 91%).

$^1$H-NMR (CDCl$_3$/TMS): δ 7.18 (m, 1H), 6.93 (m, 2H), 6.80 (m, 1H), 4.71 (m, 1H), 4.04 (m, 2H), 2.45 (d, 1H), 0.98 (t, 9H), 0.67 (q, 6H).

Example 2

5-Phenyl-(3S)-triethylsilyloxy-1-pentyne

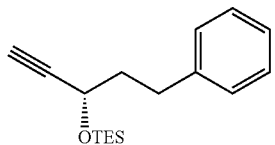

The titled compound was obtained from 5-phenyl-(3S)-hydroxy-1-pentyne as an oil in 88% yield according to the same procedure as described in Example 1.

$^1$H-NMR (CDCl$_3$/TMS): δ 7.39 (m, 2H), 7.29 (m, 3H), 4.47 (m, 1H), 2.89 (m, 2H), 2.53 (d, 1H), 2.12 (m, 2H), 1.08 (t, 9H), 0.77 (q, 6H).

Example 3

(3S)-Triethylsilyloxy-1-Octyne

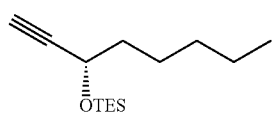

The titled compound was obtained from (3S)-hydroxy-1-Octyne as an oil in 95% yield according to the same procedure as described in Example 1.

Example 4

(1E)-Tributylstannyl-(3S)-triethylsilyloxy-1-octene

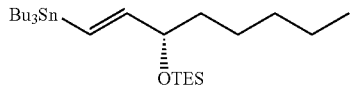

To a stirred mixture of 20 g (78.6 mmol) of (3S)-triethylsilyloxy-1-octyne and 150 mg of azo-bis(isobutyronitrile) was added 30 ml (113 mmol) of tri-n-butyltin hydride using a syringe under nitrogen atmosphere. The mixture was heated to about 130° C., stirred for 2 h, and then cooled to room temperature. Excessive tri-n-butyltin hydride was removed by vacuum distillation at about 70° C. (0.05 mmHg). The product was then obtained at about 165° C. (0.05 mmHg) under vacuum distillation as 36.5 g of a colorless liquid in a yield of 87%.

$^1$H NMR δ 4.05 (br m, 1H, C-3 H), 6.0 (m, 2H, olefin); $^{13}$C NMR δ 152.2, 126.6, 77.0, 38.2, 32, 29.3, 27.4, 25.1, 22.8, 14.1, 13.7, 9.6, 6.9, 5.1.

Example 5

5-Phenyl-(1E)-tributylstannyl-(3S)-triethylsilyloxy-1-pentene

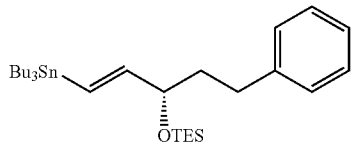

The titled compound was obtained from 5-phenyl-(3S)-triethylsilyloxy-1-pentyne as an oil in 82% yield according to the same procedure as described in Example 4.

$^1$H-NMR (CDCl$_3$/TMS): δ 7.33 (m, 2H), 7.23 (m,3H), 5.90~6.21 (m, 2H), 4.15 (q, 1H), 2.74 (m, 2H), 1.88 (m, 2H), 1.57 (m, 2H), 1.30~1.80 (m, 12H), 0.90~1.08 (m, 24H), 0.67 (q, 6H).

Example 6

(1E)-Tributylstannyl-4-[3-(Trifluoromethyl)phenoxy]-(3R)-triethylsilyloxy-1-butene

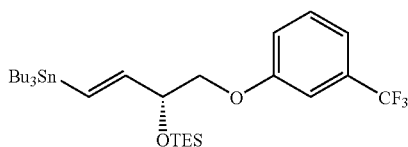

The titled compound was obtained from 4-[3-(trifluoromethyl)phenoxy]-(3R)-triethylsilyloxy-1-butyne as an oil in 74% yield according to the same procedure as described in Example 4.

$^1$H-NMR (CDCl$_3$/TMS): δ 7.22 (m, 1H), 6.96 (m, 2H), 6.81 (m, 1H), 5.90~6.21 (m, 2H), 4.49 (m, 1H), 3.90 (d, 2H).

Example 7

(1E)-Iodo-(3S)-triethylsilyloxy-1-octene

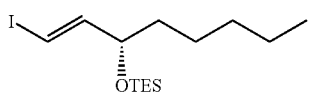

To a stirred solution of 5.3 g (1E)-tributylstannyl-(3S)-triethylsilyloxy-1-octene in 75 ml ether was added 2.5 g iodine. The solution was allowed to be stirred at room temperature for about 2 hours and concentrated to dry under vacuum evaporation. The crude product was further purified by column chromatography on silica gel using a mixture of hexane and ether as a gradient eluent. The yield of the titled compound was 2.2 g (63%).

$^1$H-NMR (CDCl$_3$/TMS): δ 6.49 (dd, 1H), 6.19 (d, 1H), 4.04 (q, 1H), 1.20~1.70 (m, 8H), 0.93 (t, 9H), 0.83 (t, 3H), 0.57 (q, 6H).

Example 8

Ethyl(1R,2R,3R)-3-hydroxy-2-[(3S)-hydroxy-1-octenyl]-5-oxo-cyclopentane acetate

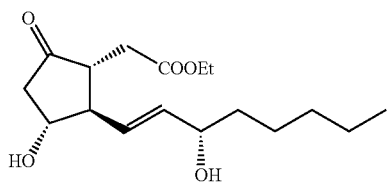

A 250-ml three-necked flask was flame dried and allowed to be cooled. Copper cyanide (2.7 g, 30 mmol) and 40 ml anhydrous tetrahydrofuran (THF) were added to the reaction flask, followed by dropwise addition of 40 ml methyllithium (1.5M in ethyl ether) at about −10° C. After stirring the reaction mixture for 30 minutes, a solution of (1E)-tributylstannyl-(3S)-triethylsilyloxy-1-octene (15.9 g, 30 mmol) in 20 ml anhydrous tetrahydrofuran was added. The reaction mixture was allowed to be stirred at room temperature for 3 hours. Then, the reaction mixture was brought to −70° C. A solution of ethyl(3R)-triethylsilyoxy-5-oxo-1-cyclopenten-1-acetate (6.3 g, 21 mmol) in 20 ml anhydrous tetrahydrofuran was added to the reaction mixture. The reaction was stirred at −70° C. for 30 minutes and quenched with 500 ml saturated aqueous ammonium chloride containing 50 ml ammonium hydroxide. The reaction mixture was phase separated and the aqueous layer was extracted with ethyl acetate. The organic layers were combined and dried over anhydrous magnesium sulfate. The solid was filtered off. The solvent was evaporated off under vacuum. The residue was further dissolved in 100 ml acetone and 20 ml water, followed by addition of 0.5 g p-toluenesulfonic acid monohydrate. The reaction solution was stirred at room temperature for 1 hour and further subjected to vacuum evaporation until two separate layers were formed. 150 ml ethyl acetate was added to the reaction and the reaction was allowed to be phase separated. The organic layer was washed with saturated sodium bicarbonate solution and brine, dried over anhydrous magnesium sulfate, and evaporated to dryness. The crude product was purified by chromatography on silica gel using a mixture of hexane and ethyl acetate as a gradient eluent. Yield of the titled compound was 5.83 g (89%) containing a trace amount of 15-epimer. The 15-epimer can be removed by crystallization of the titled compound from ether/hexane. 4.2 g titled compound was obtained in a crystalline form (white to off-white powder). MP: 62° C.

$^1$H-NMR (CDCl$_3$/TMS): δ 5.69 (m, 1H), 5.57 (m, 1H), 4.15 (m, 4H), 3.38 (br, 1H), 2.80 (dd, 1H), 2.15~2.65 (m, 6H), 1.20~1.84 (m, 10H), 0.90 (t, 3H); $^{13}$C-NMR (CDCl$_3$/TMS): δ 213.22, 172.31, 138.26, 131.06, 73.42, 72.86, 61.55, 54.85, 51.64, 45.96, 37.95, 32.36, 32.35, 25.79, 23.24, 14.81, 14.68.

Example 9

Benzyl(1R,2R,3R)-3-hydroxy-2-[(3S)-hydroxy-1-octenyl]-5-oxo-cyclopentane acetate

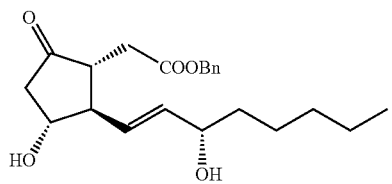

A solution of (1E)-Iodo-(3S)-triethylsilyloxy-1-octene (35.4 g) in 200 ml ether was cooled to −70° C. and 60 ml of 1.6M n-butyllithium solution was added. The solution thus obtained was labeled as Solution A and allowed to be stirred at −70° C. for 2 hours. To a dry flask was added CuCN (8.3 g) and ether (50 ml). The solution was cooled to −20° C., to which a 1.5M solution of methyllithium in ether (61 ml) was added. The solution mixture was labeled as Solution B and allowed to be stirred for another 30 minutes. Subsequently, Solution B was cooled to −70° C. to which previously prepared vinyllithium solution (Solution A) was added. The mixture was stirred for 1 hour while maintaining the temperature at about −70° C. Benzyl(3R)-triethylsilyloxy-5-oxo-1-cyclopenten-1-acetate (26.2 g) in 50 ml of ether was added to the reaction mixture. After being stirred for another 20 minutes, the reaction mixture was poured into a mixture of 9/1 (v/v) saturated aqueous NH$_4$Cl/NH$_4$OH solution to be phase separated. The aqueous layer was extracted with ethyl acetate. The organic layers were combined and dried over anhydrous magnesium sulfate. The solid was filtered off, and the solvent was evaporated off under vacuum. The residue was dissolved in 300 ml acetone and 50 ml water, followed by addition of 2 g p-toluenesulfonic acid monohydrate. The reaction solution was stirred at room temperatures for 1 hour and concentrated until two separate layers were observed. 150 ml ethyl acetate was added for extraction. The organic layer was further washed with saturated sodium bicarbonate solution and brine, dried over anhydrous magnesium sulfate, and evaporated to dryness. The liquid residue was purified by chromatography on silica gel using a mixture of hexane and ethyl acetate as a gradient eluent. The titled compound was obtained in a crystalline form. Yield: 74%. MP: 74° C.

$^1$H-NMR (CDCl$_3$/TMS): δ 7.39 (m, 5H), 5.52~5.71 (m, 2H), 5.12 (dd, 2H), 4.05~4.20 (m, 2H), 3.36 (s, 1H), 2.79 (dd, 1H), 2.64 (m, 2H), 2.38~2.55 (m, 3H), 2.34 (dd, 1H), 1.10~1.80 (m,7H), 0.89 (t, 3H). $^{13}$C-NMR (CDCl$_3$/TMS): δ 213.05, 172.11, 138.37, 136.24, 130.24, 129.29, 129.08, 128.70, 73.37, 72.62, 67.35, 54.81, 51.63, 45.93, 37.93, 32.35, 25.80, 23.29, 14.60.

Example 10

2-Naphthyl(1R,2R,3R)-3-hydroxy-2-[(3S)-hydroxy-1-octenyl]-5-oxo-cyclopentane acetate

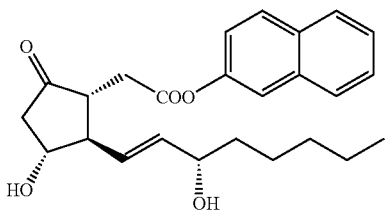

According to the same procedure as described in Example 9 except that the equimolar substrate used in the reaction was 2-naphthyl(3R)-tetrahydropyranyloxy-5-oxo-1-cyclopenten-1-acetate instead of benzyl(3R)-triethylsilyoxy-5-oxo-1-cyclopenten-1-acetate. The titled compound was prepared and obtained in a crystalline form. Yield: 63%.

$^1$H-NMR (CDCl$_3$/TMS): δ 7.87 (m, 3H), 7.58 (s, 1H), 7.50 (m, 2H), 7.25 (m, 1H), 5.76 (m, 2H), 4.21 (m, 2H), 2.87 (m, 3H), 2.61 (m, 2H), 2.42 (m, 1H), 1.20~1.80 (m, 8H), 0.87 (t, 3H).

Example 11

Benzyl(1R,2R,3R)-3-hydroxy-2-[5-phenyl-(3S)-hydroxy-1-pentenyl]-5-oxo-cyclopentane acetate

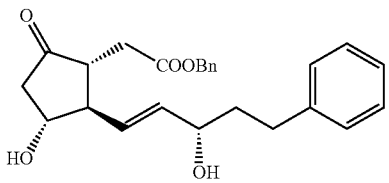

A 100 ml flask equipped with a stirrer bar was charged with zirconocene chloride hydride (1.29 g, 5 mmol) and sealed with a septum. The flask was evacuated with a vacuum pump and purged with argon, which was repeated for 3 times. THF (15 ml) was subsequently added to the flask and the mixture was stirred to generate a white slurry to which 5-phenyl-(3S)-triethylsilyloxy-1-pentyne (1.37 g, 5 mmol) was added. The mixture was stirred for 30 minutes and cooled to −70° C. Upon addition of ethereal MeLi (3.5 ml, 5 mmol), a bright yellow solution was formed. Concurrently, lithium 2-thienyl-cyanocuprate (20 ml, 0.25M in THF) was added to the zirconium solution. The mixture was stirred for 15 minutes at −70° C. and benzyl(3R)-triethylsilyloxy-5-oxo-1-cyclopenten-1-acetate (0.90 g, 2.5 mmol) in ether (5 ml) was added. After 10 minutes, the mixture was quenched with 40 ml of 10% NH$_4$OH in saturated NH$_4$Cl aqueous solution. The product was extracted with 50 ml of ether for 3 times and dried over MgSO$_4$. The solution was then filtered and the solvent was removed by vacuum evaporation. The liquid residue was dissolved in 20 ml acetone and 4 ml water, followed by addition of 0.2 g p-toluenesulfonic acid monohydrate. The reaction solution was stirred at room temperature for 1 hour and concentrated until two separate layers were observed. 30 ml ethyl acetate was added for extraction and phase separation. The organic layer was washed with saturated sodium bicarbonate solution and brine, dried over anhydrous magnesium sulfate, and subjected to vacuum evaporation for removal of the solvent until dryness. The liquid residue was further purified by chromatography on silica gel using a mixture of hexane and ethyl acetate as a gradient eluent. The titled compound was obtained in a crystalline form. Yield: 82%. MP: 81° C.

$^1$H-NMR (CDCl$_3$/TMS): δ 7.17~7.42 (m, 10H), 5.56~5.78 (m, 2H), 5.1 (dd, 2H), 4.13 (m, 2H), 2.16~2.87 (m, 6H), 1.80~2.10 (m, 2H); $^{13}$C-NMR(CDCl$_3$/TMS): δ 212.87, 172.07, 142.13, 138.15, 135.63, 129.28, 129.17, 129.09, 129.06, 128.83, 126.70, 72.70, 72.39, 67.39, 54.71, 51.62, 46.04, 39.52, 32.43, 32.42.

Example 12

(1'R,2'S,5'R)-Menthyl(1R,2R,3R)-3-hydroxy-2-[(3S)-hydroxy-1-octenyl]-5-oxo-cyclopentane acetate

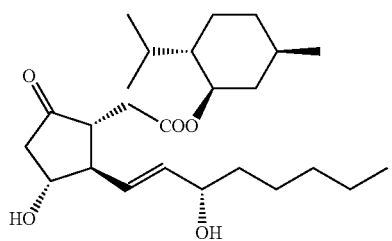

According to the same procedure as described in Example 8 except that the equimolar of the substrate used in the reaction was (1'R,2'S,5'R)-menthyl(3R)-triethylsilyoxy-5-oxo-1-cyclopenten-1-acetate instead of ethyl(3R)-triethylsilyoxy-5-oxo-1-cyclopenten-1-acetate. The titled compound can be prepared and obtained in a crystalline form. Yield: 62%. MP: 96° C.

$^1$H-NMR (CDCl$_3$/TMS): δ 5.59 (m, 2H), 4.59 (m, 1H), 4.05 (m, 2H), 2.71 (m, 1H), 2.49 (m, 3H), 2.28 (m, 2H).

Example 13

3-Ethoxycarbonylphenyl(1R,2R,3R)-3-hydroxy-2-[(3S)-hydroxy-1-octenyl]-5-oxo-cyclopentane acetate

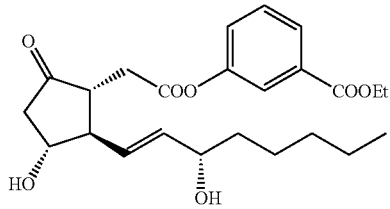

According to the same procedure as described in Example 8 except that the equimolar of the substrate used in the reaction was 3-ethoxycarbonylphenyl(3R)-triethylsilyloxy-5-oxo-1-cyclopenten-1-acetate instead of ethyl(3R)-triethylsilyoxy-5-oxo-1-cyclopenten-1-acetate. The titled compound can be prepared and obtained in Yield 68%. $^1$H-NMR (CDCl$_3$/TMS): δ 7.94 (d, 1H), 7.76 (s, 1H), 7.47 (t, 1H), 7.31 (m, 1H), 5.75 (dd, 1H), 5.63 (dd, 1H), 4.41 (q, 2H), 4.17 (m, 2H), 2.86 (m, 3H), 2.57 (m, 2H), 2.37 (dd, 1H), 1.57 (m, 1H), 1.51 (m, 1H), 1.43 (t, 3H), 1.29 (m, 6H), 0.90 (t, 3H).

Example 14

2-Cyanoethyl(1R,2R,3R)3-hydroxy-2-[(3S)-hydroxy-1-octenyl]-5-oxo-cyclopentane acetate

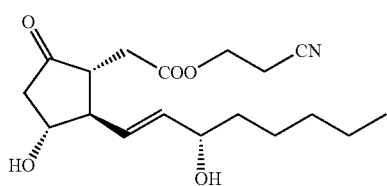

According to the same procedure as described in Example 8 except that the equimolar of the substrate used in the reaction was 2-cyanoethyl(3R)-triethylsilyloxy-5-oxo-1-cyclopenten-1-acetate instead of ethyl(3R)-triethylsilyoxy-5-oxo-1-cyclopenten-1-acetate. The titled compound can be prepared and obtained in a crystalline form. Yield: 72%. MP: 54° C. $^1$H-NMR (CDCl$_3$/TMS): δ 5.66 (m, 1H), 5.55 (m, 1H), 4.29 (m, 2H), 4.10 (m, 2H), 2.79 (dd, 1H), 2.74 (t, 2H), 2.59 (m, 2H), 2.44 (m, 2H), 2.33 (dd, 1H), 1.58 (m, 1H), 1.49 (m, 1H), 1.31 (m, 6H), 0.91 (t, 3H).

Example 15

Ethyl(1R,2R,3R)3-hydroxy-2-[5-phenyl-(3S)-hydroxy-1-pentenyl]-5-oxo-cyclopentane acetate

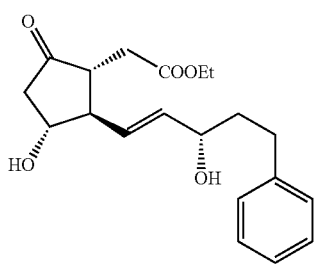

According to the same procedure as described in Example 8 except that the equimolar of the substrate used in the reaction was (1E)-tributylstannyl-5-phenyl-(3R)-triethylsilyloxy-1-pentene instead of (1E)-tributylstannyl-(3S)-triethylsilyloxy-1-octene. The titled compound can be prepared and obtained in 68% yield. $^1$H-NMR (CDCl$_3$/TMS): δ 7.30 (m, 2H), 7.22 (m, 3H), 5.71 (dd, 1H), 5.58 (dd, 1H), 4.11 (m, 4H), 3.34 (brs, 2H), 2.30~2.90 (m, 6H), 1.70~1.95 (m, 2H), 1.25 (t, 3H).

Example 16

4-Morpholineethyl(1R,2R,3R)-3-hydroxy-2-[(3S)-hydroxy-1-octenyl]-5-oxo-cyclopentane acetate

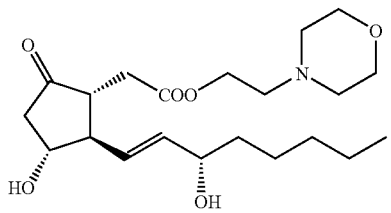

According to the same procedure as described in Example 8 except that the equimolar of the substrate used in the reaction was 4-morpholineethyl(3R)-triethylsilyloxy-5-oxo-1-cyclopenten-1-acetate instead of ethyl(3R)-triethylsilyoxy-5-oxo-1-cyclopenten-1-acetate, the titled compound can be prepared and obtained in 70% yield. $^1$H-NMR (CDCl$_3$/TMS): δ 5.64 (dd, 1H), 5.54 (dd, 1H), 4.21 (m, 4H), 4.08 (m, 2H), 3.72 (t, 4H), 2.77 (dd, 1H), 2.63 (t, 2H), 2.57 (t, 1H), 2.52 (brs, 4H), 2.37 (m, 2H), 1.56 (m, 1H), 1.47 (m, 1H), 1.30 (m, 6H), 0.90 (t, 3H).

Example 17

2-Naphthyl(1R,2R,3R)3-hydroxy-2-[5-phenyl-(3S)-hydroxy-1-pentenyl]-5-oxo-cyclopentane acetate

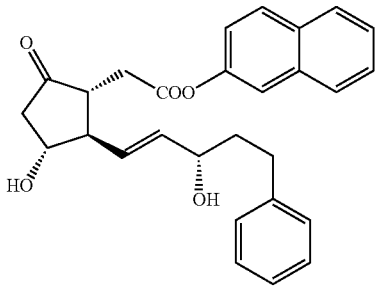

According to the same procedure as described in Example 15 except that equimolar of the substrate used in the reaction was 2-naphthyl(3R)-triethylsilyloxy-5-oxo-1-cyclopenten-1-acetate instead of ethyl(3R)-triethylsilyoxy-5-oxo-1-cyclopenten-1-acetate. The titled compound can be prepared and obtained in a crystalline form. Yield: 72%. MP: 123° C.

Example 18

(1'R,2'S,5'R)-Menthyl(1R,2R,3R)-3-hydroxy-2-[5-phenyl-(3S)-hydroxy-1-pentenyl]-5-oxo-cyclopentane acetate

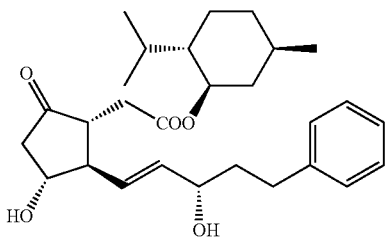

According to the same procedure as described in Example 15 except that the equimolar of the substrate used in the reaction was (1'R,2'S,5'R)-menthyl(3R)-triethylsilyoxy-5-oxo-1-cyclopenten-1-acetate instead of ethyl(3R)-triethylsilyoxy-5-oxo-1-cyclopenten-1-acetate. The titled compound can be prepared and obtained in a crystalline form. Yield: 67%. MP: 115° C.

Example 19~20

Ethyl(1R,2R,3R)3-hydroxy-2-[5-phenyl-(3R)-hydroxy-pentanyl]-5-oxo-cyclopentane acetate

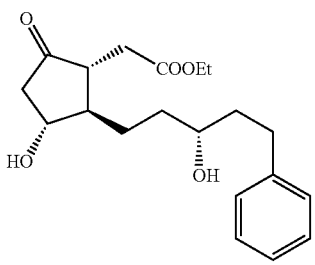

Example 19

1.25 g of (3S)-3-(tert-butyldimethylsilyloxy)-5-bromo-1-phenylpentane was dissolved in ether (20 ml) and cooled to −70° C. T-BuLi (1.7M in pentane, 4.3 ml) was added dropwise and the mixture was stirred for 30 minutes. (2-Thienyl)Cu(CN)Li (0.25M, 30 ml) was added dropwise thereto. The reaction solution was stirred for 1 hour and ethyl(3R)-triethylsilyloxy-5-oxo-1-cyclopenten-1-acetate (0.74 g, 2.5 mmol) in ether (5 ml) was added. After 10 minutes, the mixture was quenched with 40 ml of 10% $NH_4OH$ in saturated $NH_4Cl$ aqueous solution. The product was extracted with 50 ml of ether for 3 times and dried over $MgSO_4$. The solution was then filtered and the solvent was removed by vacuum evaporation. The liquid residue was dissolved in dichloromethane (20 ml) and added with hydrofluoride solution in pyridine (2.5 ml) at 0° C., and stirred for 3 hours. Upon completion of the reaction, the reaction mixture was poured into a saturated sodium bicarbonate aqueous solution and the aqueous phase was further extracted with ethyl acetate twice. The organic layers were combined, dried over $MgSO_4$, filtered, and concentrated. The residue was purified by column chromatography to give the titled compound in a Yield of 48%.

Example 20

To a stirred solution of ethyl(1R,2R,3R)3-hydroxy-2-[5-phenyl-(3S)-hydroxy-1-pentenyl]-5-oxo-cyclopentane acetate (1 g) in ethyl acetate (10 ml) was added 5% Pd—C catalyst (0.2 g). The solution was stirred for 30 hours under hydrogen environment. The solution was filtered to obtain a filtrate which is further concentrated to dryness. The crude product was subjected to further purification by flash column chromatography (over silica gel with eluting solvents being ethylacetate:hexane=1:1) to obtain the titled compound as a colorless oil (0.68 g)

$^1$H-NMR ($CDCl_3$/TMS): δ 7.31 (m, 2H), 7.22 (m, 3H), 4.15 (q, 2H), 3.65~4.3 (m, 2H).

Example 21

Ethyl(1R,2R,3R)3-triethylsilyloxy-2-[(3S)-triethylsilyloxy-1-octenyl]-5-oxo-cyclopentaneacetate

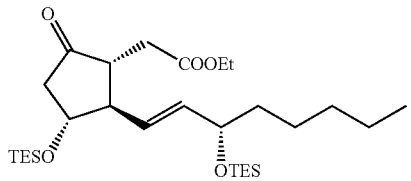

Ethyl3-hydroxy-2-(3-hydroxy-1-octenyl)-5-oxo-cyclopentaneacetate (12.5 g, 40 mmol) was dissolved in 100 ml ethyl acetate, added with 6.8 g imidazole, and stirred until the reaction system became homogeneous. 14.7 ml of triethylsilyl chloride was added slowly into the reaction mixture. The stirred reaction mixture was brought to room temperature and stirred overnight. The reaction mixture was filtered to obtain a filtrate. Subsequently, the reaction mixture was washed with 30 ml saturated sodium bicarbonate aqueous solution twice, further washed with brine, dried over anhydrous magnesium sulfate, filtered, and concentrated to obtain the crude product (20.2 g).

Example 22~31

(3aR,4R,5R,6aS)-hexahydro-5-hydroxy-4-[(1E,3S)-3-hydroxy-1-octenyl]-2H-cyclopenta[β]furan-2-one

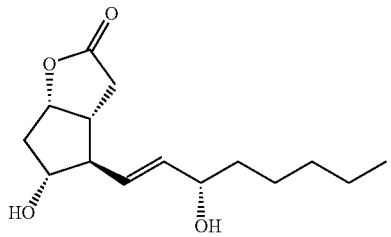

$^1$H-NMR (CDCl$_3$/TMS): δ 5.62 (m, 1H), 5.48 (m, 1H), 4.31 (m, 1H), 3.96~4.17 (m, 2H), 0.89 (t, 3H).

Example 22

Benzyl(1R,2R,3R)-3-hydroxy-2-[(3S)-hydroxy-1-octenyl]-5-oxo-Cyclopentane acetate (20 g, 49 mmol) in 200 ml THF was cooled by dry ice methanol bath to about −70° C. Then 1.0M lithium tri-(sec-butyl)-borohydride (49 ml) was added dropwise into the solution. The reaction was stirred for 2 hours and quenched by 100 ml saturated ammonium chloride aqueous solution. After phase separation, the aqueous layer was extracted twice with ethyl acetate. The organic layers were combined, washed with brine, dried over anhydrous magnesium sulfate, and evaporated under reduced pressure. The concentrate was purified by column chromatography on silica gel. The titled compound was obtained in 82% yield.

Example 23

According to the same procedure as described in Example 22 except that the equimolar of the substrate used in the reaction was ethyl(1R,2R,3R)3-hydroxy-2-[(3S)-hydroxy-1-octenyl]-5-oxo-cyclopentaneacetate instead of benzyl(1R,2R,3R)-3-hydroxy-2-[(3S)-hydroxy-1-octenyl]-5-oxo-cyclopentaneacetate. The titled compound can be prepared and obtained in 75% Yield.

Example 24

According to the same procedure as described in Example 22 except that the equimolar of the substrate used in the reaction was 2-naphyl(1R,2R,3R)-3-hydroxy-2-[(3S)-hydroxy-1-octenyl]-5-oxo-cyclopentaneacetate instead of benzyl(1R,2R,3R)3-hydroxy-2-[(3S)-hydroxy-1-octenyl]-5-oxo-cyclopentaneacetate. The titled compound can be prepared and obtained in 63% Yield.

Example 25

According to the same procedure as described in Example 22 except that the equimolar of the substrate used in the reaction was menthyl(1R,2R,3R)-3-hydroxy-2-[(3S)-hydroxy-1-octenyl]-5-oxo-cyclopentaneacetate instead of benzyl(1R,2R,3R)3-hydroxy-2-[(3S)-hydroxy-1-octenyl]-5-oxo-cyclopentaneacetate. The titled compound can be prepared and obtained in 69% Yield.

Example 26

According to the same procedure as described in Example 22 except that the equimolar of the substrate used in the reaction was 4-morpholineethyl(1R,2R,3R)-3-hydroxy-2-[(3S)-hydroxy-1-octenyl]-5-oxo-cyclopentaneacetate instead of benzyl(1R,2R,3R)-3-hydroxy-2-[(3S)-hydroxy-1-octenyl]-5-oxo-Cyclopentane acetate. The titled compound can be prepared and obtained in 67% Yield.

Example 27

According to the same procedure as described in Example 22 except that the equimolar of the substrate used in the reaction was 3-ethoxycarbonylphenyl(1R,2R,3R)-3-hydroxy-2-[(3S)-hydroxy-1-octenyl]-5-oxo-cyclopentaneacetate instead of benzyl(1R,2R,3R)-3-hydroxy-2-[(3S)-hydroxy-1-octenyl]-5-oxo-cyclopentaneacetate, the titled compound can be prepared and obtained in 69% Yield.

Example 28

According to the same procedure as described in Example 22 except that the equimolar of the substrate used in the reaction was 2-cyanoethyl(1R,2R,3R)-3-hydroxy-2-[(3S)-hydroxy-1-octenyl]-5-oxo-cyclopentaneacetate instead of Benzyl(1R,2R,3R)-3-hydroxy-2-[(3S)-hydroxy-1-octenyl]-5-oxo-cyclopentane acetate. The titled compound can be prepared and obtained in 76% Yield.

Example 29

According to the same procedure as described in Example 22 except that the equimolar of the reducing agent used in the reaction was sodium tri-sec-butylborohydride instead of lithium tri-sec-butylborohydride. The titled compound can be prepared and obtained in 69% Yield.

Example 30

According to the same procedure as described in Example 22 except that the equimolar of the reducing agent used in the reaction was diisobutylaluminum hydride instead of lithium tri-sec-butylborohydride. The titled compound can be prepared and obtained in 42% Yield.

Example 31

According to the same procedure as described in Example 22 except that the equimolar of the reducing agent used in the reaction was lithium tri-tert-butoxyaluminum hydride instead of lithium tri-sec-butylborohydride. The titled compound can be prepared and obtained in 57% Yield.

Example 32

(3aR,4R,5R,6aS)-hexahydro-5-triethylsilyloxy-4-[(1E,3S)-3-triethylsilyloxy-1-octenyl]-2H-cyclopenta[β]furan-2-one

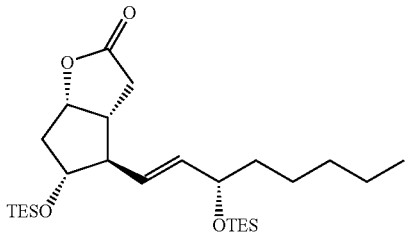

According to the same procedure as described in Example 22 except that the equimolar of the substrate used in the reaction was ethyl(1R,2R,3R)-3-triethylsilyoxy-2-[(3S)-triethylsilyloxy-1-octenyl]-5-oxo-cyclopentaneacetate instead of ethyl(1R,2R,3R)-3-hydroxy-2-[(3S)-hydroxy-1-octenyl]-5-oxo-cyclopentaneacetate. The title compound can be prepared and obtained in 95% Yield.

Example 33~36

(3aR,4R,5R,6aS)-hexahydro-5-hydroxy-4-[(1E,3S)-5-phenyl-3-hydroxy-1-pentenyl]-2H-cyclopenta[β]furan-2-one

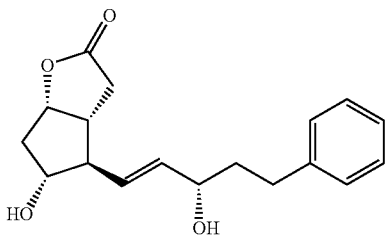

Example 33

According to the same procedure as described in Example 22 except that the equimolar of the substrate used in the reaction was ethyl(1R,2R,3R)-3-hydroxy-2-[5-phenyl-(3S)-hydroxy-1-pentenyl]-5-oxo-cyclopentane acetate instead of benzyl(1R,2R,3R)-3-hydroxy-2-[(3S)-hydroxy-1-octenyl]-5-oxo-cyclopentaneacetate. The titled compound can be prepared and obtained in 75% Yield.

Example 34

According to the same procedure as described in Example 22 except that the equimolar of the substrate used in the reaction was 2-naphathyl(1R,2R,3R)-3-hydroxy-2-[5-phenyl-(3S)-hydroxy-1-pentenyl]-5-oxo-cyclopentane acetate instead of benzyl(1R,2R,3R)-3-hydroxy-2-[(3S)-hydroxy-1-octenyl]-5-oxo-cyclopentaneacetate. The titled compound can be prepared and obtained in 68% Yield.

Example 35

According to the same procedure as described in Example 22 except that the equimolar of the substrate used in the reaction was (1′R,2′S,5′R)-menthyl(1R,2R,3R)-3-hydroxy-2-[5-phenyl-(3S)-hydroxy-1-pentenyl]-5-oxo-cyclopentane acetate instead of benzyl(1R,2R,3R)-3-hydroxy-2-[(3S)-hydroxy-1-octenyl]-5-oxo-cyclopentaneacetate. The titled compound can be prepared and obtained in 77% Yield.

Example 36

According to the same procedure as described in Example 22 except that the equimolar of the substrate used in the reaction was benzyl(1R,2R,3R)-3-hydroxy-2-[5-phenyl-(3S)-hydroxy-1-pentenyl]-5-oxo-cyclopentane acetate instead of benzyl(1R,2R,3R)-3-hydroxy-2-[(3S)-hydroxy-1-octenyl]-5-oxo-cyclopentaneacetate. The titled compound can be prepared and obtained in 78% Yield.

$^1$H-NMR (CDCl$_3$/TMS): δ 7.04~7.28 (m, 5H), 5.57 (m, 1H), 5.39 (m, 1H), 4.81 (m, 1H), 4.03 (m, 1H), 3.87 (m, 1H), 1.58~2.85 (m, 10H); $^{13}$C-NMR (CDCl$_3$/TMS): δ 177.47, 142.21, 137.13, 130.85, 129.16, 129.10, 125.88, 83.10, 77.95, 72.60, 55.88, 43.17, 40.52, 35.38, 34.83, 32.41.

Example 37~40

(3aR,4R,5R,6aS)-hexahydro-5-hydroxy-4-[5-phenyl-(3R)-hydroxy-pentanyl]-2H-cyclopenta[β]furan-2-one

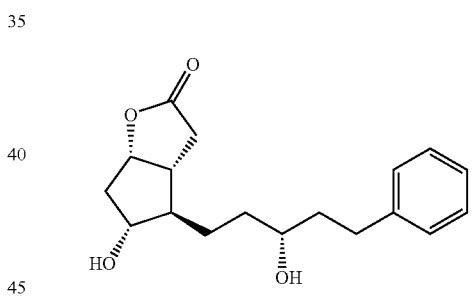

$^1$H-NMR (CDCl$_3$/TMS): δ 0.85~1.95 (m, 9H), 2.30 (m, 2H), 2.50 (m, 1H), 2.68 (m, 1H), 2.80 (m, 2H), 3.63 (m, 1H), 4.03 (m, 1H), 4.94 (m, 1H), 7.15~7.42 (m, 5H)

Example 37

According to the same procedure as described in Example 22 except that the equimolar of the substrate used in the reaction is ethyl(1R,2R,3R)-3-hydroxy-2-[5-phenyl-(3R)-hydroxy-pentanyl]-5-oxo-cyclopentane acetate instead of benzyl(1R,2R,3R)-3-hydroxy-2-[(3S)-hydroxy-1-octenyl]-5-oxo-cyclopentaneacetate. The titled compound can be prepared and obtained in a crystalline form (yield: 75%).

Example 38

To a solution of (3aR,4R,5R,6aS)-hexahydro-5-hydroxy-4-[(1E,3S)-5-phenyl-3-hydroxy-1-pentenyl]-2H-cyclopenta[β]furan-2-one (10 g) in ethyl acetate (100 ml) was added 10% Pt-C catalyst (1 g) and sodium hydroxide (0.2 g). The solution was stirred under hydrogen atmosphere for 18 hours.

After filtration, the filtrate was concentrated in vacuum to remove the solvent. The crude product was subjected to purification using flash column chromatography (over silica gel with developing solvent being ethyl acetate:hexane=1:1). The titled compound was obtained in a crystalline form (yield 72%).

Example 39

To a solution of (3aR,4R,5R,6aS)-hexahydro-5-hydroxy-4-[(1E,3S)-5-phenyl-3-hydroxy-1-pentenyl]-2H-cyclopenta[β]furan-2-one (1 g) in ethyl acetate (10 ml) was added 5% Pd—C catalyst (0.2 g) and sodium hydroxide (0.05 g). The solution was stirred under hydrogen atmosphere overnight. After filtration, the filtrate was concentrated by vacuum evaporation. The crude product was subjected to flash column chromatography (on silica gel, eluted with ethyl acetate:hexane=1:1). The titled compound was obtained in a crystalline form (yield 78%).

Example 40

To a solution of (3aR,4R,5R,6aS)-hexahydro-5-hydroxy-4-[(1E,3S)-5-phenyl-3-hydroxy-1-pentenyl]-2H-cyclopenta[β]fuiran-2-one (1 g) in ethyl alcohol (10 ml) was added with Raney nickel catalyst (0.5 g) and sodium hydroxide (0.1 g). The solution was stirred under hydrogen atmosphere for 10 hours. After filtration, the filtrate was concentrated by vacuum evaporation. The crude product was subjected to flash column chromatography (on silica gel eluted with ethyl acetate:hexane=1:1). The titled compound was obtained in a crystalline form (yield 68%). MP: 68~72° C.; $^1$H-NMR (CDCl$_3$ITMS): δ 7.15~7.42 (m, 5H), 4.94 (m, 1H), 4.03 (m, 1H), 3.63 (m, 1H), 2.80 (m, 2H), 2.68 (m, 1H), 2.50 (m, 1H), 2.30 (m, 2H), 0.85~1.95 (m, 9H); $^{13}$C-NMR(CDCl$_3$/TMS): δ 178.04, 142.41, 129.19, 129.07, 126.68, 84.45, 78.32, 72.03, 54.72, 43.95, 41.35, 39.79, 36.65, 35.89, 32.73, 29.67.

Example 41

(3aR,4R,5R,6aS)-hexahydro-5-hydroxy-4-[(3R)-hydroxy-4-(3-trifluoromethyl)phenoxy-1-butenyl]-2H-cyclopenta[β]furan-2-one

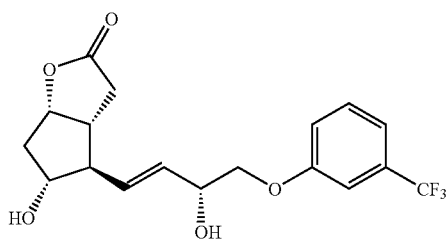

Ethyl(1R,2R,3R)-3-hydroxy-2-[(3R)-hydroxy-4-(3-trifluoromethyl)phenoxy-1-butenyl]-5-oxo-cyclopenane acetate was prepared according to a similar procedure as described in Example 11 except that the equimolar of the substrates used in the reaction were ethyl(3R)-triethylsilyloxy-5-oxo-1-cyclopenten-1-acetate and 4-[3-(trifluoromethyl)phenoxy]-(3R)-triethylsilyloxy-1-butyne instead of benzyl(3R)-triethylsilyloxy-5-oxo-1-cyclopenten-1-acetate and 5-phenyl-(3S)-triethylsilyloxy-1-pentyne. The crude product thus obtained was subjected to reduction/lactonization directly according to the same procedure as described in Example 22. The titled compound can be prepared and obtained in a yield of 25%.
$^1$H-NMR (CDCl$_3$/TMS): δ 7.41 (m, 1H), 7.25 (m, 1H), 7.14 (s, 1H), 7.09 (m, 1H), 5.75 (m, 2H), 4.93 (q, 1H), 4.57 (s, 1H), 4.04 (m, 2H), 3.92(m, 1H), 2.28~2.82 (m, 4H), 1.92~2.18 (m, 2H).

Example 42

(3aR,4R,5R,6aS)-hexahydro-5-tert-butyldimethylsilyloxy-4-[(1E,3S)-3-tert-butyldimethylsilyloxy-1-octenyl]-2H-cyclopenta[β]furan-2-one

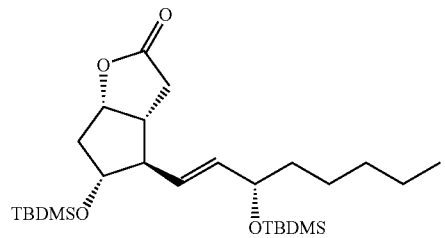

(3aR,4R,5R,6aS)-hexahydro-5-hydroxy-4-[(1E,3S)-3-hydroxy-1-octenyl]-2H-cyclopenta[β]furan-2-one (10.7 g, 40 mmol) was dissolved in 100 ml ethyl acetate, added with 8.2 g imidazole, and stirred until the reaction system became homogeneous. 15.7 g tert-butyldimethylsilyl chloride dissolved in 50 ml ethyl acetate was gradually added to the reaction mixture. The reaction mixture was stirred at room temperature overnight. The reaction mixture was filtered to obtain a filtrate. Subsequently, the reaction mixture was washed with 50 ml saturated aqueous sodium bicarbonate solution twice, further washed with brine, dried over anhydrous magnesium sulfate, filtered, and concentrated to obtain the crude product. The crude product was crystallized from hexane at −70° C. (cold dry ice bath temperatures), filtered, and washed with cold hexane. The solid was dried to give the titled compound as a white solid. MP: 74° C. (14.3g).
$^1$H-NMR (CDCl$_3$/TMS): δ 5.47 (dd, 1H), 5.35 (dd, 1H), 4.93 (td, 1H), 4.02 (q, 1H), 3.96 (q, 1H), 2.73 (m, 1H), 2.62 (m, 1H), 2.45 (m, 2H), 2.22 (m, 1H), 1.95 (m, 1H), 1.44 (m, 1H), 1.38 (m, 1H), 1.27 (m, 6H), 0.82~0.88 (m, 3H), 0.86 (s, 9H), 0.85 (s, 9H), 0.02 (m, 12H).

Example 43

(3aR,4R,5R,6aS)-Hexahydro-5-triethylsilyoxy-4-[5-phenyl-(3R)-triethylsilyloxy-pentanyl]-2H-cyclopenta[β]furan-2-one

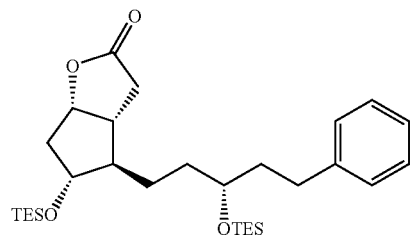

(3aR,4R,5R,6aS)-hexahydro-5-hydroxy-4-[5-phenyl-(3R)-triethylsilyloxy-pentanyl]-2H-cyclopenta[β]furan-2-one (12.2 g, 40 mmol) was dissolved in 120 ml ethyl acetate, added with 8.2 g imidazole, and stirred until the reaction system became homogeneous. 15.7g triethylsilyl chloride was added to the reaction mixture and the reaction mixture was stirred at room temperature for 30 minutes. The reaction mixture was filtered to obtain a filtrate, which was then washed twice with 50 ml saturated aqueous sodium bicarbonate solution, and washed with 50 ml brine, dried over anhydrous magnesium sulfate, filtered, and concentrated to obtain the crude product (21 g).

Example 44

Preparation of Latanoprost

To a stirred solution of (3aR,4R,5R,6aS)-hexahydro-5-triethylsilyoxy-4-[5-phenyl-(3R)-triethylsilyloxy-pentanyl]-2H-cyclopenta[β]furan-2-one (21 g, 39.4 mol) in dry toluene (250 ml) at −78° C. was added a solution of diisobutylaluminum hydride (60 ml, 20% in hexane) dropwise. After being stirred for 2 hours, the reaction mixture was poured into a solution of 2M sodium hydrogensulfate and stirred for 30 minutes. The aqueous phase was extracted twice with toluene (2×100 ml). The combined organic layers was washed with brine, dried over anhydrous magnesium sulfate, and evaporated to dryness. The crude corresponding lactol was obtained as a colorless oil. Potassium tert-butoxide (27 g, 240 mmol) was added to a suspension of 4-carboxybutyl-triphenylphosphonium bromide (53 g, 120 mmol) in 500 ml THF. The mixture was cooled to less than −10° C. and the crude lactol obtained above was added. The mixture was stirred for 18 hours and 200 ml saturated aqueous ammonium chloride solution was added. Upon phase separation, the organic as well as the aqueous layers were separately collected. The pH of the aqueous phase was adjusted to 6 with 2M sodium hydrogen sulfate solution and then the aqueous layer was extracted with 500 ml ethyl acetate twice. The combined organic layers were dried over anhydrous magnesium sulfate, filtered, and evaporated under vacuum. The liquid residue was further dissolved in 120 ml DMF and added with 15 g 2-iodopropane, followed by addition of 10 g $K_2CO_3$. The reaction solution was stirred at room temperature for 12 hours, then diluted with 500 ml ethyl acetate, and washed with water (2×100 ml). The organic layer was dried over anhydrous magnesium sulfate, filtered, concentrated, and purified by column chromatography to obtain the protected Latanoprost. The protected Latanoprost was dissolved in 100 ml of THF and 10 ml of water, added with 1 ml of conc. HCl, stirred at room temperatures for 30 minutes. 50 ml saturated aqueous sodium bicarbonate solution was then added. The aqueous layer was extracted twice with ethyl acetate (100 ml). The combined organic layers were washed with brine, dried over anhydrous magnesium sulfate, and evaporated to dryness. The crude product was subjected to flash column chromatography (over silica gel eluted with ethylacetate:hexane=1:1). The titled compound was obtained as a colorless oil (5.4 g). The product was further analyzed by HPLC and about 2~3% 5-trans Latanoprost without 15-β isomer was found in the final product.

Example 45

Preparation of Dinoprost

To a stirred solution of (3aR,4R,5R,6aS)-hexahydro-5-triethylsilyloxy-4-[(1E,3S)-3-triethylsilyloxy-1-octenyl]-2H-cyclopenta[β]furan-2-one (19.9 g, 40 mol) in dry toluene (250 ml) at −78° C. was added a solution of diisobutylaluminum hydride (60 ml, 20% in hexanes) dropwise. After being stirred for 2 hours, the reaction mixture was poured into a 2M aqueous solution of sodium hydrogensulfate and stirred for 30 minutes. The aqueous layer was collected separately from the organic layer and extracted twice with toluene (100 ml). The combined organic layers was washed with brine, dried over anhydrous magnesium sulfate, and evaporated to dryness. The crude Lactol was obtained as a colorless oil. Potassium tert-butoxide (27 g, 240 mmol) was added to a suspension of 4-carboxybutyl-triphenylphosphonium bromide (53 g, 120 mmol) in 500 ml THF. The mixture was cooled to less than −10° C and the crude Lactol was added. The mixture was further stirred at less than −10° C. for 18 hours and then added with 200 ml saturated ammonium chloride solution. Upon phase separation, the aqueous layer and the organic layer were separately collected. The pH of the aqueous layer was adjusted to 4 with 2M sodium hydrogen sulfate solution and extracted twice with 500 ml ethyl acetate. The combined the organic layers was dried over anhydrous magnesium sulfate, filtered, and evaporated under vacuum. A slightly yellowish oil was thus obtained. To a stirred solution of the above obtained yellowish oil, 100 ml of THF, 10 ml of water, and 1 ml of conc. HCl were added. After being stirred at room temperature for 30 minutes, the reaction mixture was added with 50 ml saturated sodium bicarbonate solution. The aqueous layer was separately collected and extracted twice with ethyl acetate (100 ml). The combined organic layers was washed with brine, dried over anhydrous magnesium sulfate, and evaporated to dryness. Crude Prostagladin F2α (Dinoprost) thus obtained was analyzed by HPLC and about 2~3% 5-trans PGF2α without 15-β isomer was found in the final product.

We claim:

1. A process for preparing the compounds of Formula II-2, having an enantiomeric purity higher than 95% enantiomeric excess:

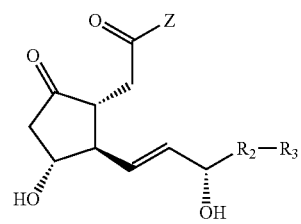

II-2 wherein Z is —$OR_1$, —$N(R_1)_2$, or —$SR_1$, wherein $R_1$ at each occurrence is independently an alkyl, an alkenyl, an alkynyl, an aryl, or an aralkyl, each of which is unsubstituted or substituted with one or more substituents selected from the group consisting of halogen, alkyl, aryl, alkoxyl, aryloxy, thioalkoxyl, thioaryloxy, alkylamino, arylamino, cyano, alkoxycarbonyl, arylcarbonyl, arylaminocarbonyl, alkylaminocarbonyl, pyridinyl, thiophenyl, furanyl, imidazolyl, morpholinyl, oxazolinyl, piperidinyl, piperazinyl, tetrahydropyranyl, pyrrolidinyl and pyrrolidinonyl;

$R_2$ is a single bond or a $C_{1-4}$-alkylene or —$CH_2O$—; and $R_3$ is a $C_{1-7}$-alkyl or an aryl or an aralkyl, each of which is unsubstituted or substituted by a $C_{1-4}$-alkyl, a halogen or a trihalomethyl;

the process comprising the steps of:
(1) reacting compounds of Formula IV having an optical purity higher then 90% enantiomeric excess:

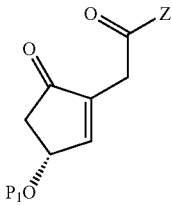

IV wherein $P_1$ is a protecting group for the hydroxyl groups, with a cuprate derived from the compound of Formula V-1, Formula V-2 or Formula V-3, each of which having an optical purity higher then 90% enantiomeric excess:

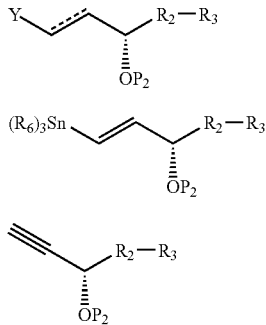

V-1

V-2

V-3 wherein Y is a halogen, $R_6$ is a lower alkyl, $R_2$ and $R_3$ are as defined above, ===== is a single bond or a double bond, and $P_2$ is a protecting group for the hydroxyl groups; to form a mixture of high optical purity compound of Formula II-1;

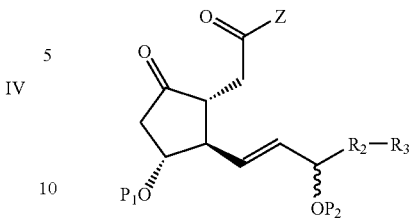

II-1

(2) deprotecting the compound of Formula II-1 to remove $P_1$ and $P_2$ in the presence of acids to form a mixture of high optical purity compound of Formula II-2 and its diastereomers; and
(3) removing the diastereomers of the compound of Formula II-2.

2. The process according to claim 1, wherein the step of removing the diastereomers comprises crystallization.

3. The process according to claim 1, wherein the protective groups for the hydroxyl groups are selected from the group consisting of methoxymethyl, methoxythiomethyl, 2-methoxyethoxymethyl, bis(2-chloroethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, triphenylmethyl, allyl, benzyl, substituted benzyl, and $SiR_a R_b R_c$ wherein $R_a$, $R_b$ and $R_c$ are each independently a $C_{1-4}$ alkyl, phenyl, benzyl, a substituted phenyl, or a substituted benzyl.

4. The process according to claim 1, wherein Z is $-OR_1$ and $R_1$ is as defined in claim 1.

5. The process according to claim 1, wherein $R_2$ and $R_3$ are selected from the group consisting of:
(i) $R_2$ is methylene and $R_3$ is n-butyl;
(ii) $R_2$ is ethylene and $R_3$ is phenyl; and
(iii) $R_2$ is $-CH_2O-$ and $R_3$ is phenyl that is substituted by halogen or trihalomethyl.

* * * * *